(12) United States Patent
Ninomiya et al.

(10) Patent No.: US 9,180,898 B2
(45) Date of Patent: Nov. 10, 2015

(54) CART FOR PORTABLE ULTRASONIC DIAGNOSTIC DEVICE AND ULTRASONIC DIAGNOSTIC UNIT

(75) Inventors: Atsushi Ninomiya, Tokyo (JP); Masaru Yokoyama, Tokyo (JP); Kazuyuki Yanase, Tokyo (JP); Masaru Ichimura, Tokyo (JP); Katsumi Usami, Tokyo (JP)

(73) Assignee: HITACHI ALOKA MEDICAL, LTD., Tokyo (JP)

(*) Notice: Subject to any disclaimer, the term of this patent is extended or adjusted under 35 U.S.C. 154(b) by 0 days.

(21) Appl. No.: 14/129,413

(22) PCT Filed: Jul. 30, 2012

(86) PCT No.: PCT/JP2012/069333
§ 371 (c)(1),
(2), (4) Date: Dec. 26, 2013

(87) PCT Pub. No.: WO2013/046907
PCT Pub. Date: Apr. 4, 2013

(65) Prior Publication Data
US 2014/0117635 A1 May 1, 2014

(30) Foreign Application Priority Data
Sep. 30, 2011 (JP) ................... 2011-217733

(51) Int. Cl.
*B62B 3/02* (2006.01)
*A61B 8/00* (2006.01)
*B62B 3/00* (2006.01)

(52) U.S. Cl.
CPC ............ *B62B 3/02* (2013.01); *A61B 8/4405* (2013.01); *A61B 8/4411* (2013.01);
(Continued)

(58) Field of Classification Search
CPC ........... A61B 2560/0456; A61B 2560/0437; A61B 8/4411; A61B 8/4427; A61B 8/4433; A61B 8/4405; B62B 2202/56
USPC ............. 280/35, 47.34, 47.35; 600/47, 437; 248/917, 918; 312/223.3
See application file for complete search history.

(56) References Cited

U.S. PATENT DOCUMENTS 6,447,451 B1 9/2002 Wing et al.
6,709,391 B2* 3/2004 Mesaros et al. ............... 600/437
(Continued)

FOREIGN PATENT DOCUMENTS

JP 05-212029 8/1993
JP 06-133970 5/1994
(Continued)

OTHER PUBLICATIONS

Extended European Search Report, dated Apr. 2, 2015, which issued during the prosecution of European Patent Application No. 12837598.7, which corresponds to the present application.

*Primary Examiner* — John Walters
*Assistant Examiner* — Brian Swenson
(74) *Attorney, Agent, or Firm* — Baker Botts L.L.P.

(57) ABSTRACT

A cart is provided for mounting a portable ultrasonic diagnostic device, the cart being small in size and having high operability, and the portable ultrasonic diagnostic device is opened and used in the state of being kept mounted on the cart. The cart has a top board 1 for placing the portable ultrasonic diagnostic device thereon, a support column 2 for supporting the top board in such a manner as movable up and down, multiple legs 3 for supporting the support column, wheels 4 respectively attached to the legs, and a unit 5 having a predetermined function. The unit 5 is placed below the top board 1 in the rear of the support column 2, and the center of gravity of the cart is positioned in the rear of the center of the support column 2. This cart has a simple configuration enabling downsizing, and it is high in operability. It is possible to open and use the portable ultrasonic diagnostic device in the state that the portable ultrasonic diagnostic device is kept mounted on the cart.

9 Claims, 16 Drawing Sheets

(52) U.S. Cl.
CPC ............ *A61B 8/4427* (2013.01); *A61B 8/4433* (2013.01); *B62B 3/008* (2013.01); *A61B 8/4209* (2013.01); *B62B 2202/56* (2013.01); *B62B 2206/06* (2013.01)

(56) References Cited

U.S. PATENT DOCUMENTS

| | | | |
|---|---|---|---|
| 7,591,786 B2* | 9/2009 | Holmberg et al. | 600/437 |
| 8,245,652 B2* | 8/2012 | Hung | 108/50.02 |
| 8,662,605 B2* | 3/2014 | McRorie et al. | 312/276 |
| 8,714,569 B2* | 5/2014 | Lu et al. | 280/35 |
| 8,721,551 B2* | 5/2014 | Tanabe | 600/459 |
| 2004/0150963 A1 | 8/2004 | Holmberg et al. | |
| 2004/0186357 A1* | 9/2004 | Soderberg et al. | 600/300 |
| 2006/0039105 A1 | 2/2006 | Smith et al. | |
| 2007/0185390 A1* | 8/2007 | Perkins et al. | 600/300 |
| 2008/0078071 A1 | 4/2008 | Gong | |
| 2010/0001149 A1* | 1/2010 | Song et al. | 248/176.1 |
| 2010/0056913 A1 | 3/2010 | Hirakui et al. | |
| 2010/0152588 A1 | 6/2010 | Ninomiya et al. | |
| 2010/0324380 A1* | 12/2010 | Perkins et al. | 600/301 |
| 2011/0042911 A1* | 2/2011 | Kozlowski et al. | 280/47.35 |
| 2012/0126503 A1* | 5/2012 | Butler et al. | 280/47.35 |

FOREIGN PATENT DOCUMENTS

| | | |
|---|---|---|
| JP | 09-028705 | 2/1997 |
| JP | 2002-542870 | 12/2002 |
| JP | 2006-518252 | 8/2006 |
| JP | 2006-519684 | 8/2006 |
| JP | 2007-006968 | 1/2007 |
| JP | 2008-089178 | 4/2008 |
| JP | 2009-131658 | 6/2009 |
| JP | 2010-057674 | 3/2010 |
| JP | 2010-057887 | 3/2010 |
| JP | 2010-264069 | 11/2010 |
| JP | 2011-036302 | 2/2011 |

* cited by examiner

CART FOR PORTABLE ULTRASONIC DIAGNOSTIC DEVICE AND ULTRASONIC DIAGNOSTIC UNIT

TECHNICAL FIELD

The present invention relates to a cart for mounting a portable ultrasonic diagnostic device thereon.

BACKGROUND ART

In recent years, a notebook PC type device is developed as a portable ultrasonic diagnostic device (FIG. 3 and FIG. 4 in the patent document 1). This type of portable ultrasonic diagnostic device is allowed to be carried by a user's hand, placed on a desk or the like, near a test object, bringing a probe into contact with the test object, so as to display an obtained ultrasonic tomographic image, and the like, on a built-in display unit.

In the patent document 1, there is disclosed a docking cart on which the portable ultrasonic diagnostic device is mounted, the docking cart being electrically connected to the portable ultrasonic diagnostic device. In addition to a display of the portable ultrasonic diagnostic device, this docking cart is provided with a dedicated display, an operating panel, and a signal processor. The signal processor of the docking cart performs operations, such as receiving image data acquired by the portable ultrasonic diagnostic device to apply image processing to the image data, and displaying an image on the display of the docking cart.

PRIOR ART DOCUMENT

Patent Document

Patent Document 1
Japanese Unexamined Patent Application Publication (Translation of PCT Application) No. 2006-519684

DISCLOSURE OF THE INVENTION

Problem to be Solved by the Invention

In order to send and receive ultrasonic waves to and from a test object, it is necessary that the portable ultrasonic diagnostic device is placed closely beside the test object. Therefore, convenience maybe remarkably enhanced, if a notebook PC type portable ultrasonic diagnostic device is mounted on a small-sized cart and moved to get close to the test object, the portable ultrasonic diagnostic device is opened and operated in the state that it is kept mounted on the cart, and a probe is extended to the test object to send and receive ultrasonic waves to and from the test object.

The docking cart described in the patent document 1 is a large sized cart being provided with a dedicated display, an operation panel, and a signal processor, for itself. Therefore, in order to be placed near the test object, large space is required closely beside the test object. On this docking cart, the portable ultrasonic diagnostic device to be mounted is inserted in the pocket-like space provided on the back side of the docking cart, in a state of being folded. Therefore, it is not possible to open and operate the portable ultrasonic diagnostic device while it is mounted on the docking cart.

An object of the present invention is to provide a cart for a portable ultrasonic diagnostic device, which is a cart for mounting the portable ultrasonic diagnostic device thereon, being small in size and high in operability, and allowing the portable ultrasonic diagnostic device to be opened and used in a state of being kept mounted on the cart.

Means to Solve the Problem

In order to achieve the object as described above, according to the present invention, there is provided a cart having a top board for placing a portable ultrasonic diagnostic device thereon, a support column for supporting the top board in such a manner as movable up and down, multiple legs for supporting the support column, wheels respectively attached to the legs, and a unit having a predetermined function, the unit being placed below the top board in the rear of the support column, and the center of gravity of the cart being positioned in the rear of the center of the support column.

Effect of the Invention

The cart of the present invention allows the portable ultrasonic diagnostic device to be placed on the upper surface of the top board, and therefore, it is possible not only to move the cart with the portable ultrasonic diagnostic device being placed, but also to open and use the portable ultrasonic diagnostic device while it is kept placed. In addition, the center of gravity of the cart is positioned in the rear, thereby reserving wide space in front. Accordingly, the operator is allowed to insert his or her knees below the top board, thereby achieving enhanced operability. Furthermore, the configuration is simple and this achieves downsizing.

MODES FOR CARRYING OUT THE INVENTION

Figure 1:
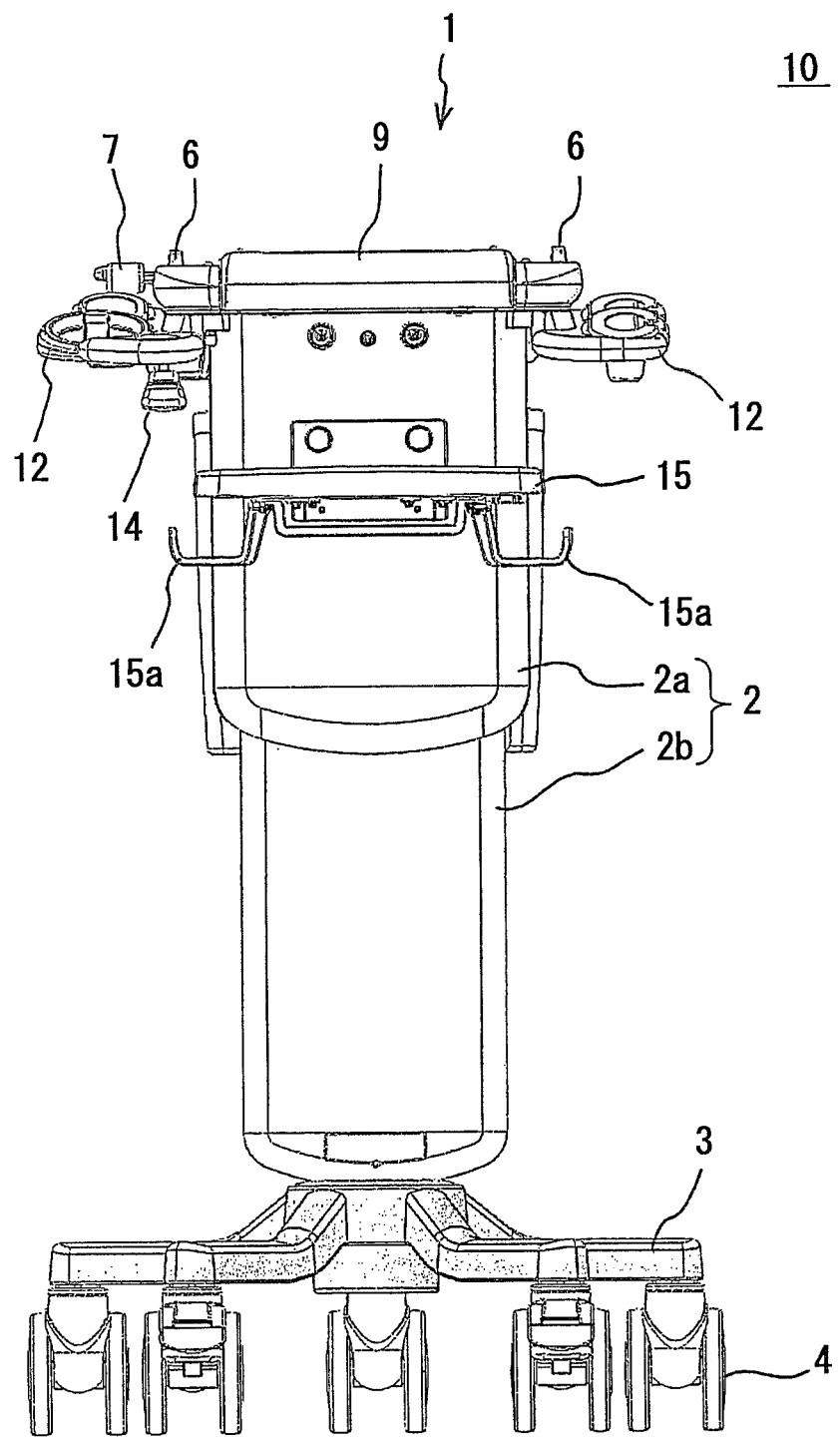
FIG. 1 is a front view of the cart 10 according to the present embodiment.

The present invention provides a cart for a portable ultrasonic diagnostic device, being provided with a top board for placing the portable ultrasonic diagnostic device thereon, a support column for supporting the top board in such a manner as movable up and down, multiple legs for supporting the support column, wheels respectively attached to the legs, and a unit having a predetermined function. The unit is placed below the top board in the rear of the support column, and the center of gravity of the cart is positioned in the rear of the center of the support column. Since the configuration of this cart is simple, it is possible to achieve downsizing and high operability. In addition, this configuration allows the portable ultrasonic diagnostic device to be opened and used while being kept mounted on the cart.

It is further possible to configure such that the cart is provided with a lifting lever for controlling up-and-down movement of the top board. Preferably, this lifting lever is arranged at a position around the top board, forward of the support column, and the center of gravity of the cart is not located at this position.

It is preferable to configure such that the number of the aforementioned legs positioned rearward of the support column is larger than the number of those positioned forward thereof. This configuration stabilizes the cart of the present invention, having its center of gravity in the rear.

The upper surface of the top board may be structured to have a convex portion that is to be engaged in a concave portion provided on the bottom surface of the portable ultrasonic diagnostic device. On this occasion, it is preferable that a hook is accommodated in the top board in such a manner as protrudable from the upper surface of the top board, the hook being engaged in the bottom surface of the portable ultrasonic diagnostic device in order to fix it on the top board.

It is further possible to configure such that a palm rest is provided in such a manner as slidable outwardly, on the front side of the top board. With this configuration, the size of the top board may be set as smaller than the bottom surface size of the portable ultrasonic diagnostic device, thereby downsizing the cart. The palm rest pulled out for the use allows the operator's wrist to be put thereon and this enhances the operability. The palm rest may take the shape that a handle is provided on the front thereof. The top board may be provided with a lock mechanism for fixing the palm rest each of the following states; the state in which the palm rest is pulled out from the top board, and the state in which the palm rest is accommodated in the top board.

It is preferable that the support column has a flat shape in which the width is larger than the depth. By way of example, the width of the support column is made equivalent to the width of the unit, thereby rendering the unit invisible from the front side, and enhancing the design ability.

It is possible to place a probe holder around the top board, for holding a probe of the portable ultrasonic diagnostic device. On this occasion, it is preferable that the probe holder is arranged in such a manner that the upper end of the probe to be held is positioned lower than the upper surface of the operating portion of the portable ultrasonic diagnostic device that is placed on the top board. This configuration prevents the probe held by the probe holder from hindering operation on the operating portion.

Mounting the portable ultrasonic diagnostic device on the aforementioned cart constitutes an ultrasonic diagnostic unit.

With reference to the drawings, a specific explanation will be provided as to the cart for the portable ultrasonic diagnostic device according to one embodiment of the present invention.

Figure 2:
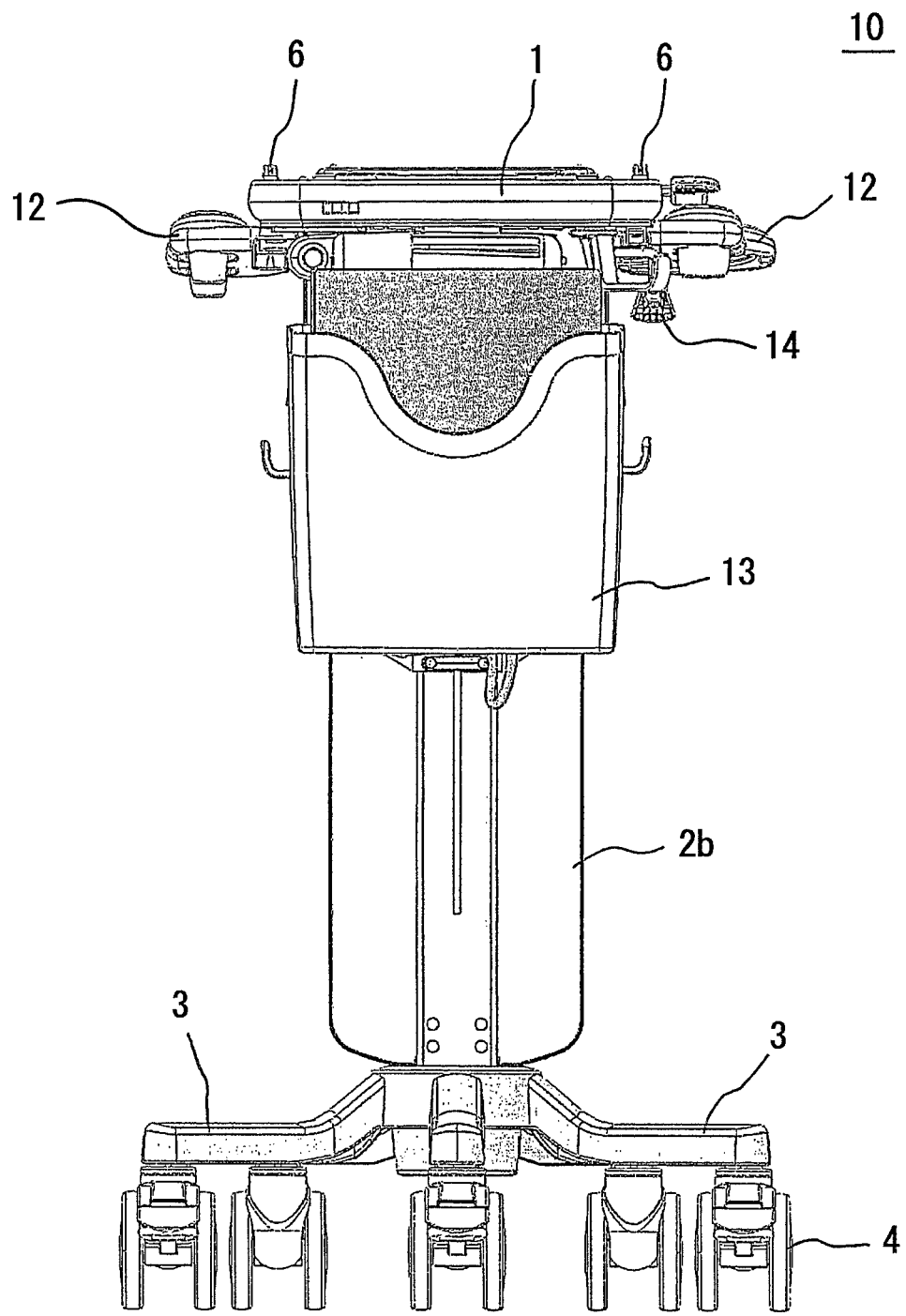
FIG. 2 is a rear view of the cart 10 as shown in FIG. 1.
Figure 3:
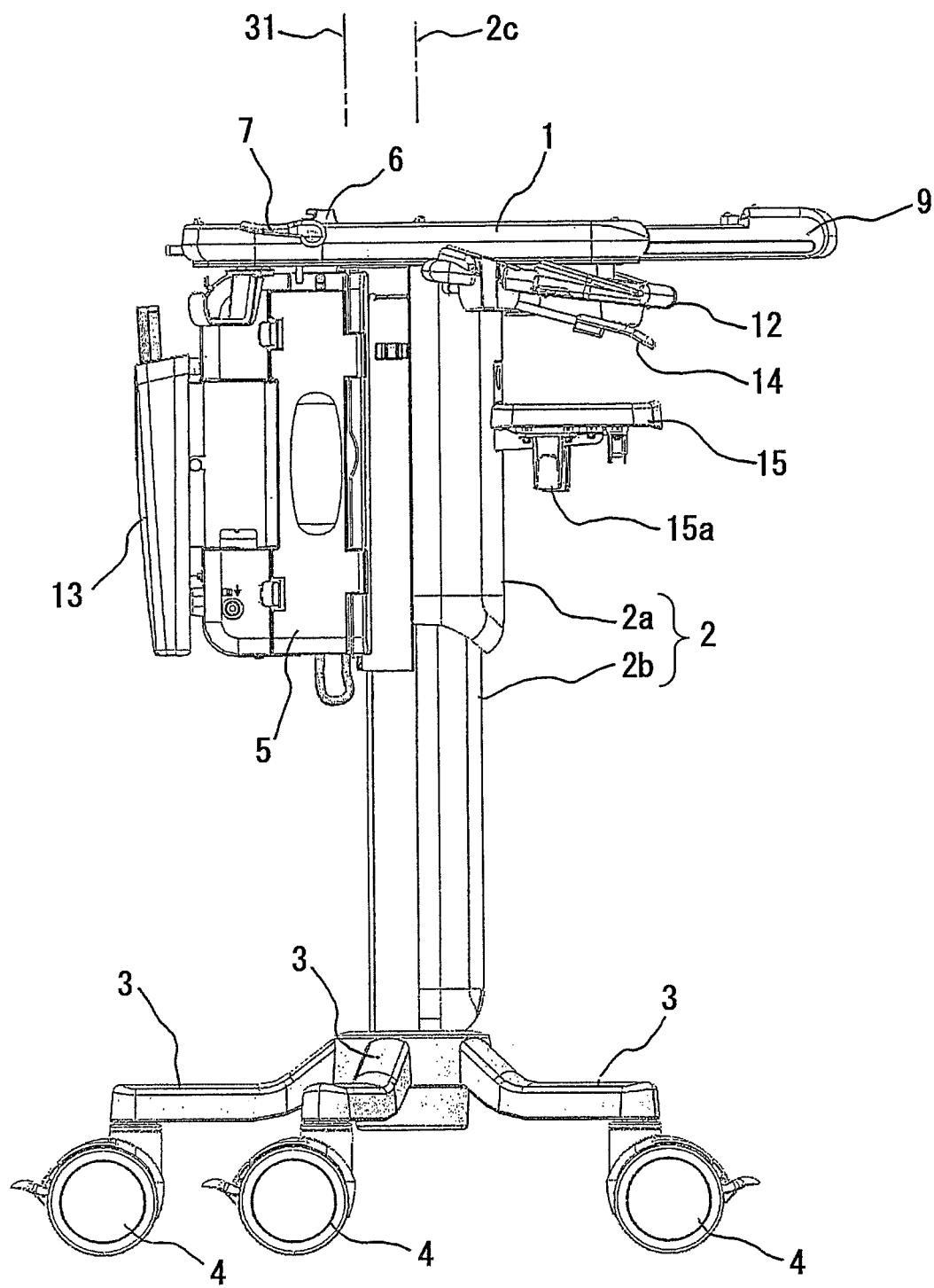
FIG. 3 is a left side view of the cart 10 as shown in FIG. 1.
Figure 4:
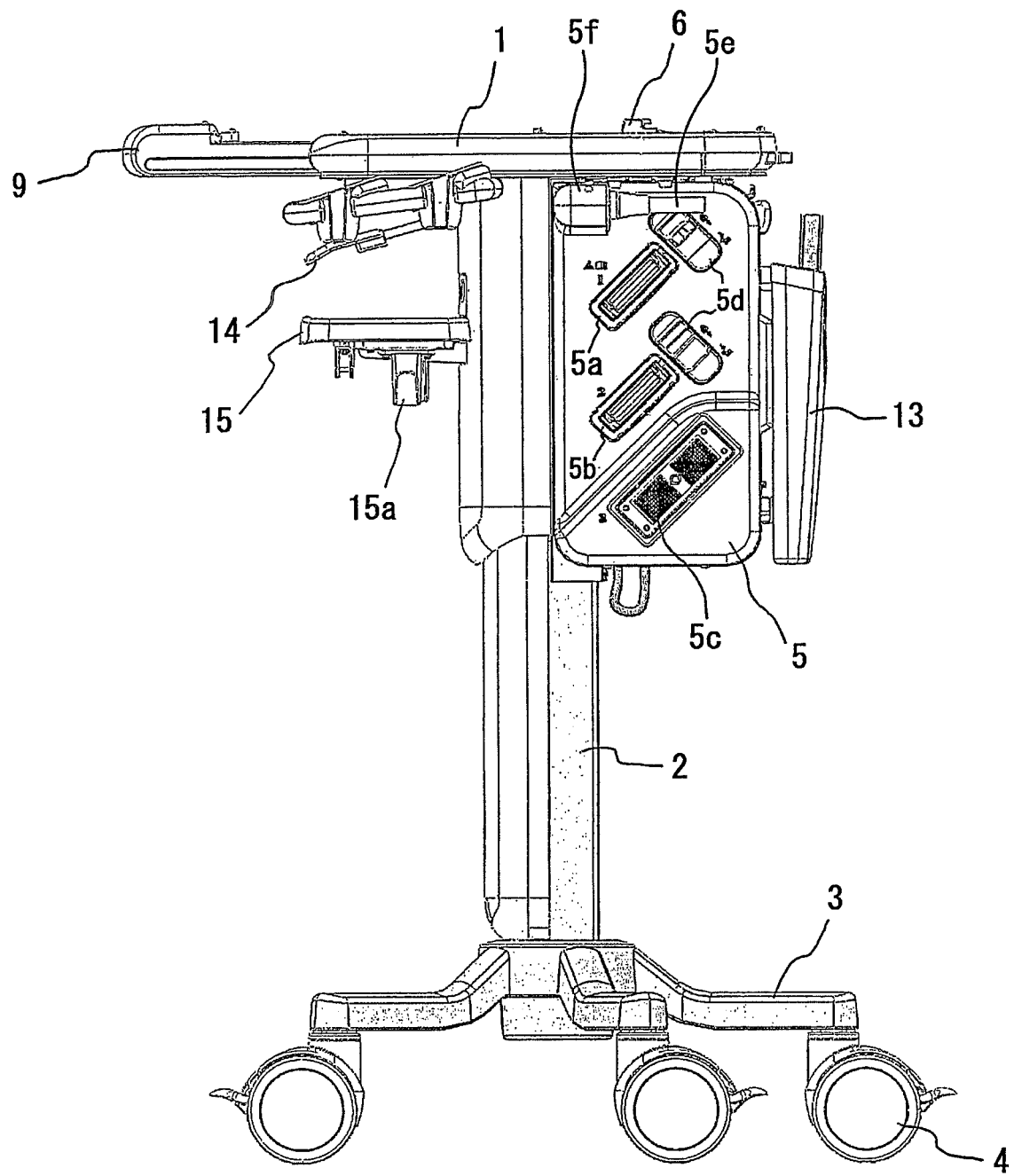
FIG. 4 is a right side view of the cart 10 as shown in FIG. 1.
Figure 5:
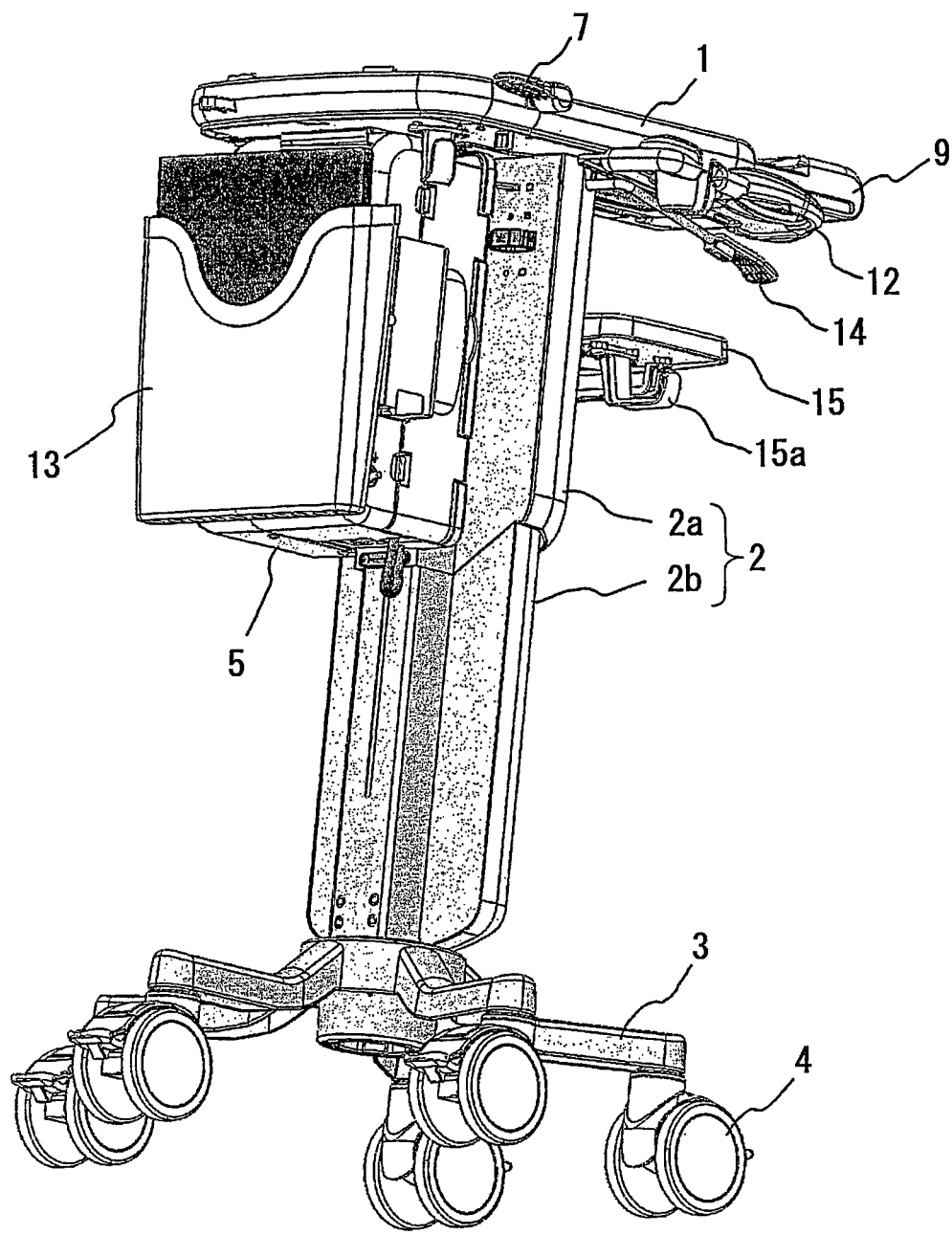
FIG. 5 is a perspective view of the rear and left sides of the cart 10 as shown in FIG. 1.
Figure 6:
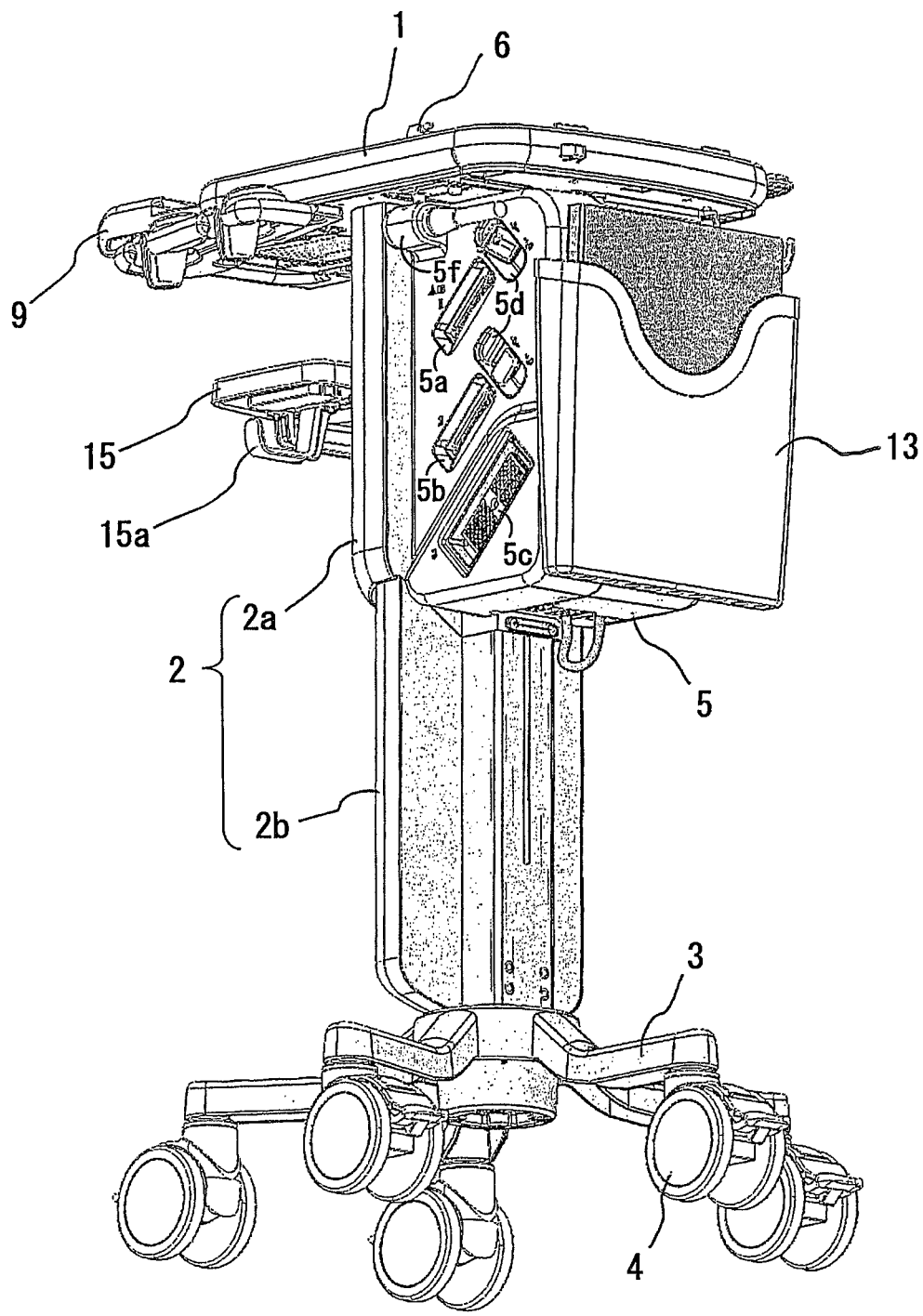
FIG. 6 is a perspective view of the rear and right sides of the cart 10 as shown in FIG. 1.
Figure 7:
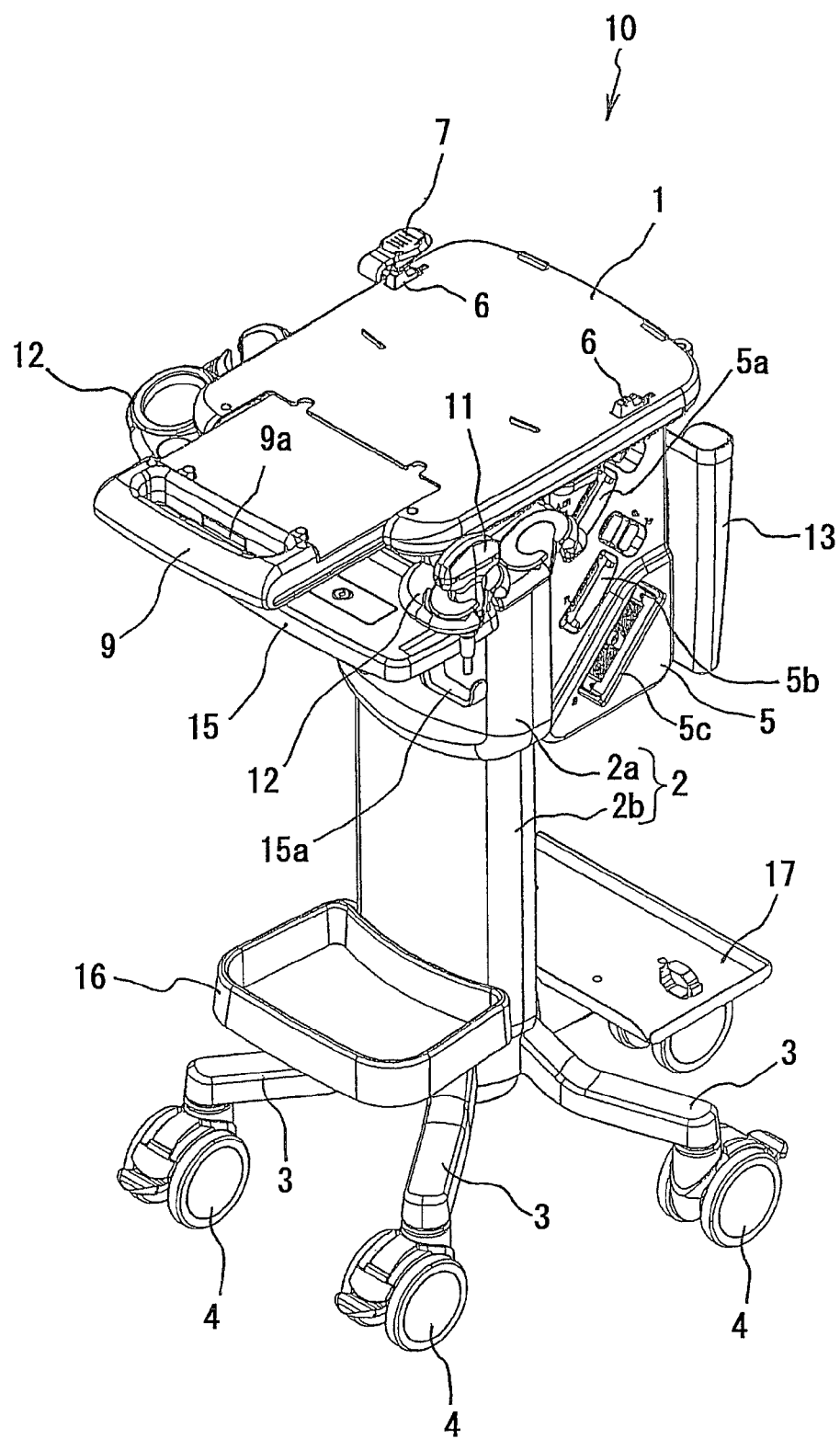
FIG. 7 is a perspective view of the upper and right sides of the cart 10 as shown in FIG. 1.
Figure 8:
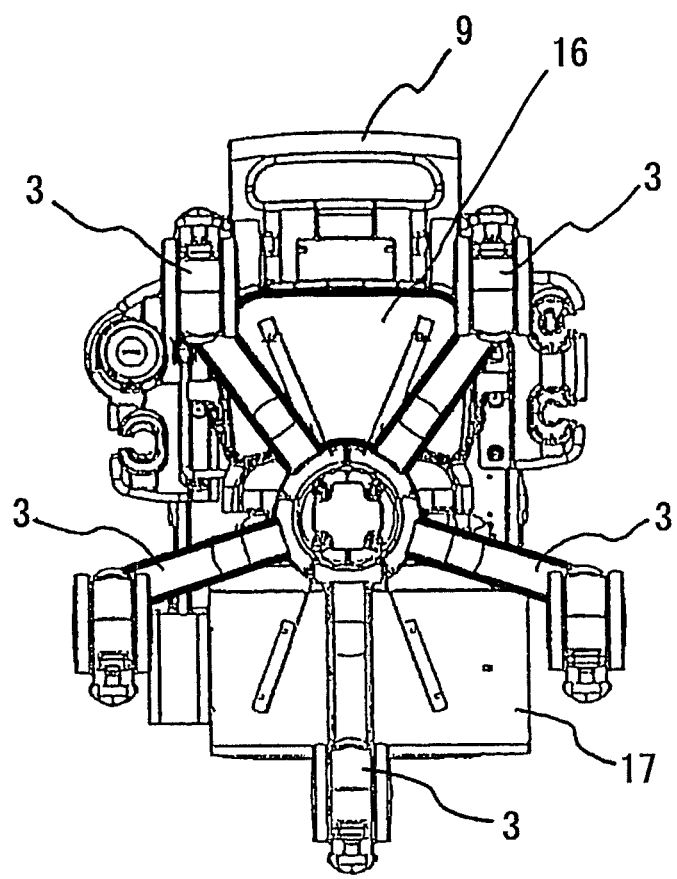
FIG. 8 is a bottom view of the cart 10 as shown in FIG. 1.
Figure 9:
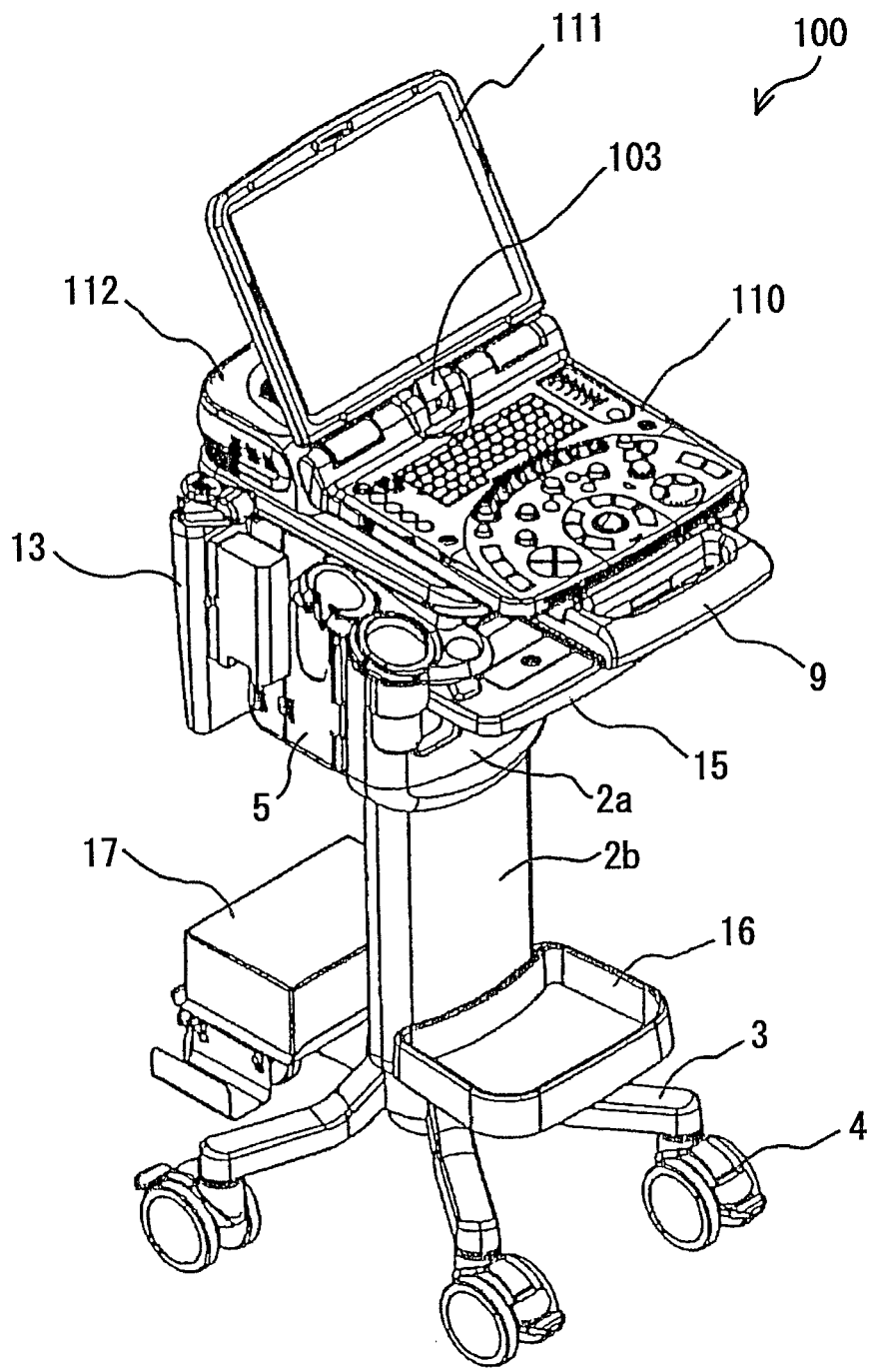
FIG. 9 is a perspective view of the cart 10 in the state that a portable ultrasonic diagnostic device 100 is mounted on the upper surface.
Figure 10:
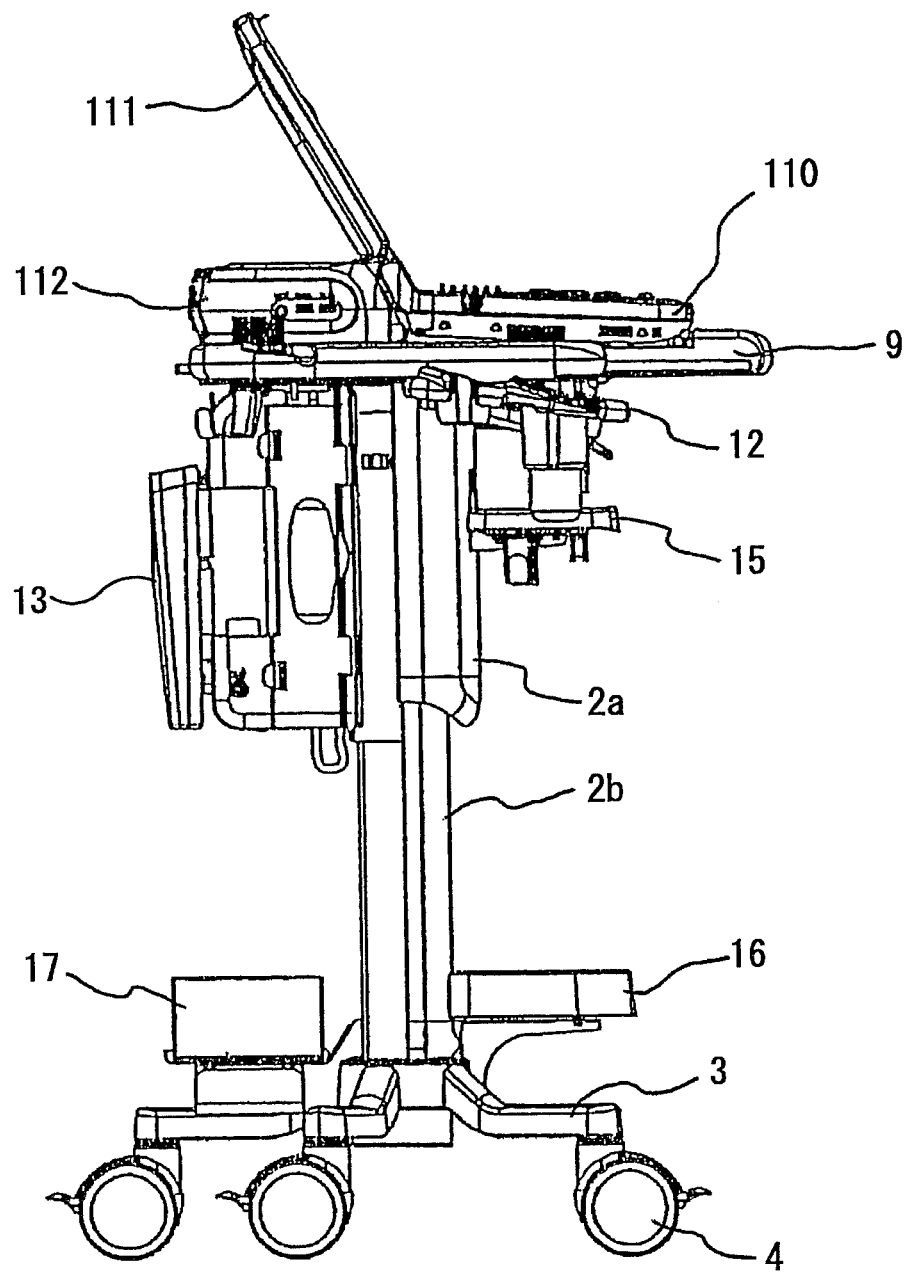
FIG. 10 is a left side view of the cart 10 as shown in FIG. 9.

Any of the figures from FIG. 1 to FIG. 13 illustrates an outside shape of the cart 10 according to the present embodiment. FIG. 1 is a front view, FIG. 2 is a rear view, FIG. 3 is a left side view, FIG. 4 is a right side view, FIG. 5 is a rear-and-left side perspective view, FIG. 6 is a rear-and-right side perspective view, FIG. 7 is an upper-and-right side perspective view, and FIG. 8 is a bottom view of the cart. FIG. 9 is a perspective view of the cart 10 in the state that the portable ultrasonic diagnostic device 100 is mounted on the upper surface, and FIG. 10 is a left side view thereof. Any of the figures from FIG. 1 to FIG. 10 illustrates the state that a palm rest 9 is pulled out, which will be described below.

Figure 11:
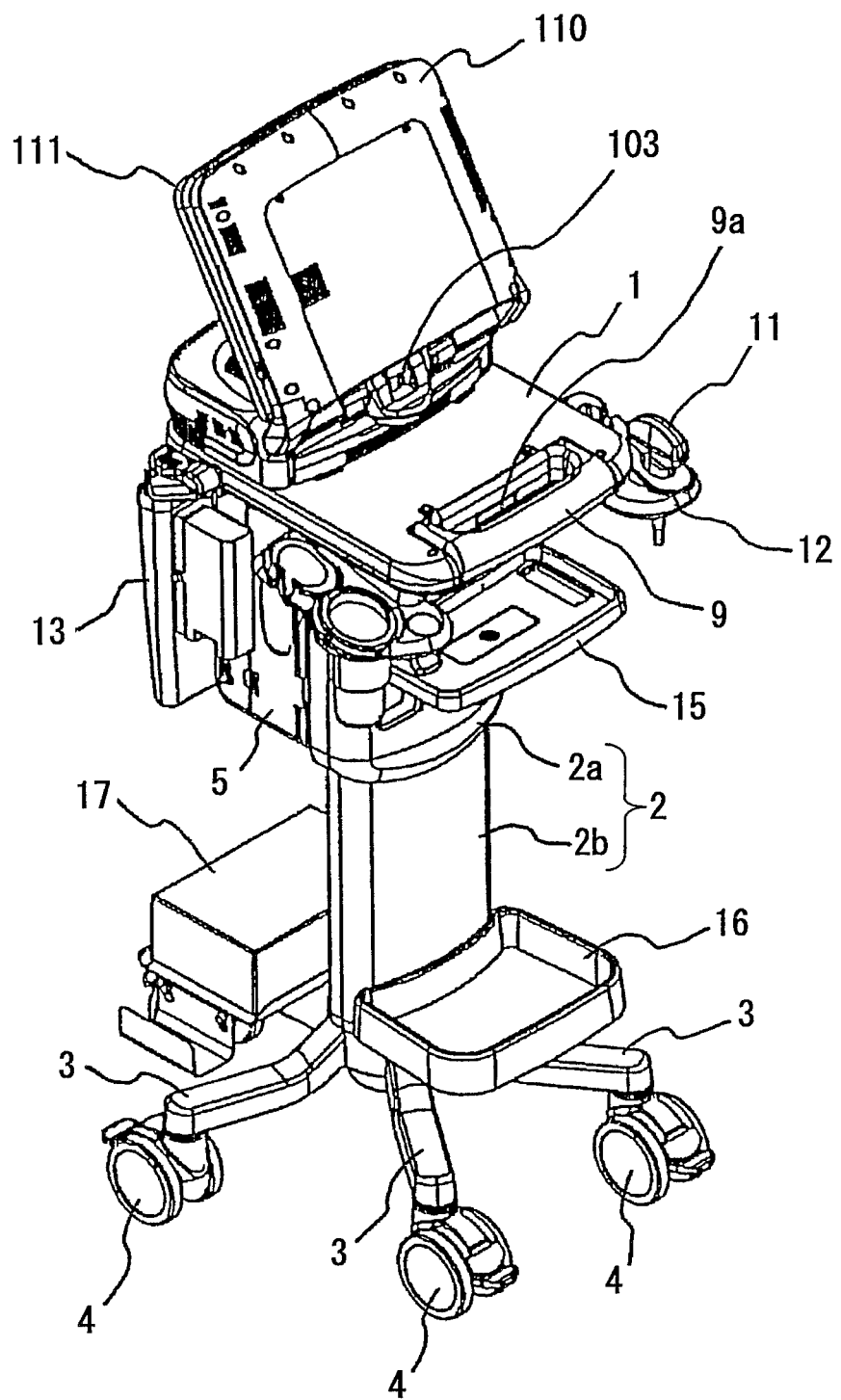
FIG. 11 is a perspective view of the cart 10 on which the portable ultrasonic diagnostic device 100 is mounted in such a manner that the operating portion 110 is raised upwardly and put together with the display 111.
Figure 12:
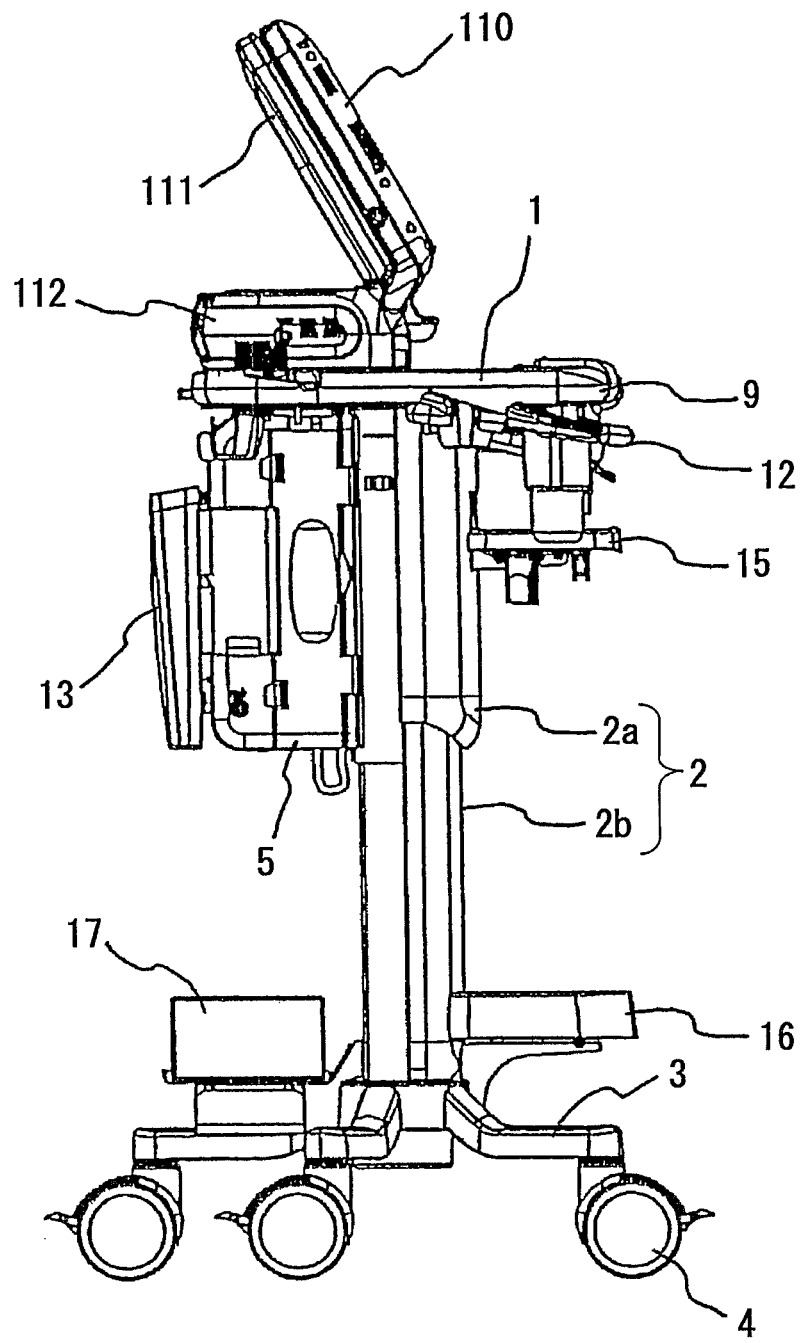
FIG. 12 is a left side view of the cart 10 as shown in FIG. 11.
Figure 13:
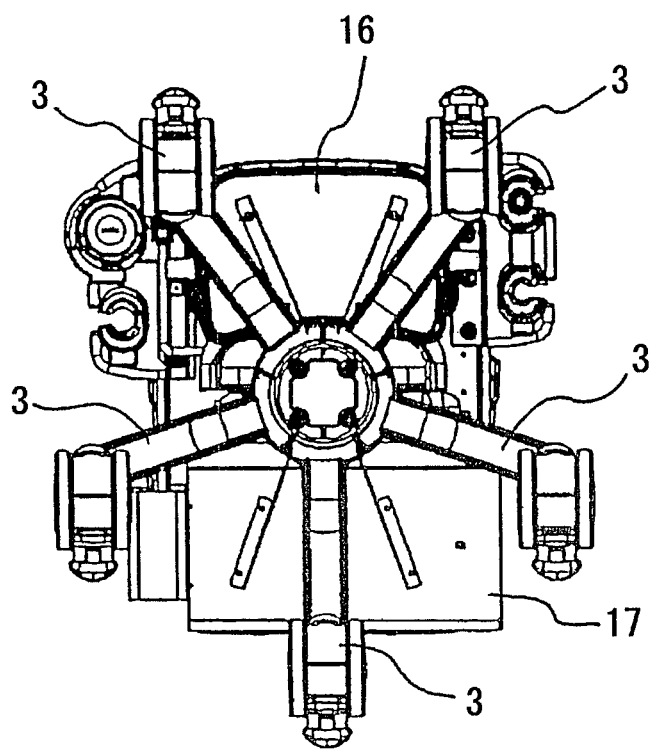
FIG. 13 is a bottom view of the cart as shown in FIG. 11.

Figures from FIG. 11 to FIG. 13 are, respectively, a perspective view, a left side view, and a bottom view of the portable ultrasonic diagnostic device 100 being mounted, in the position that the operating portion 110 is raised upwardly to be put together with placed over the display 111. In any of the figures from FIG. 11 to FIG. 13, the palm rest 9 is not pulled out.

Figure 14:
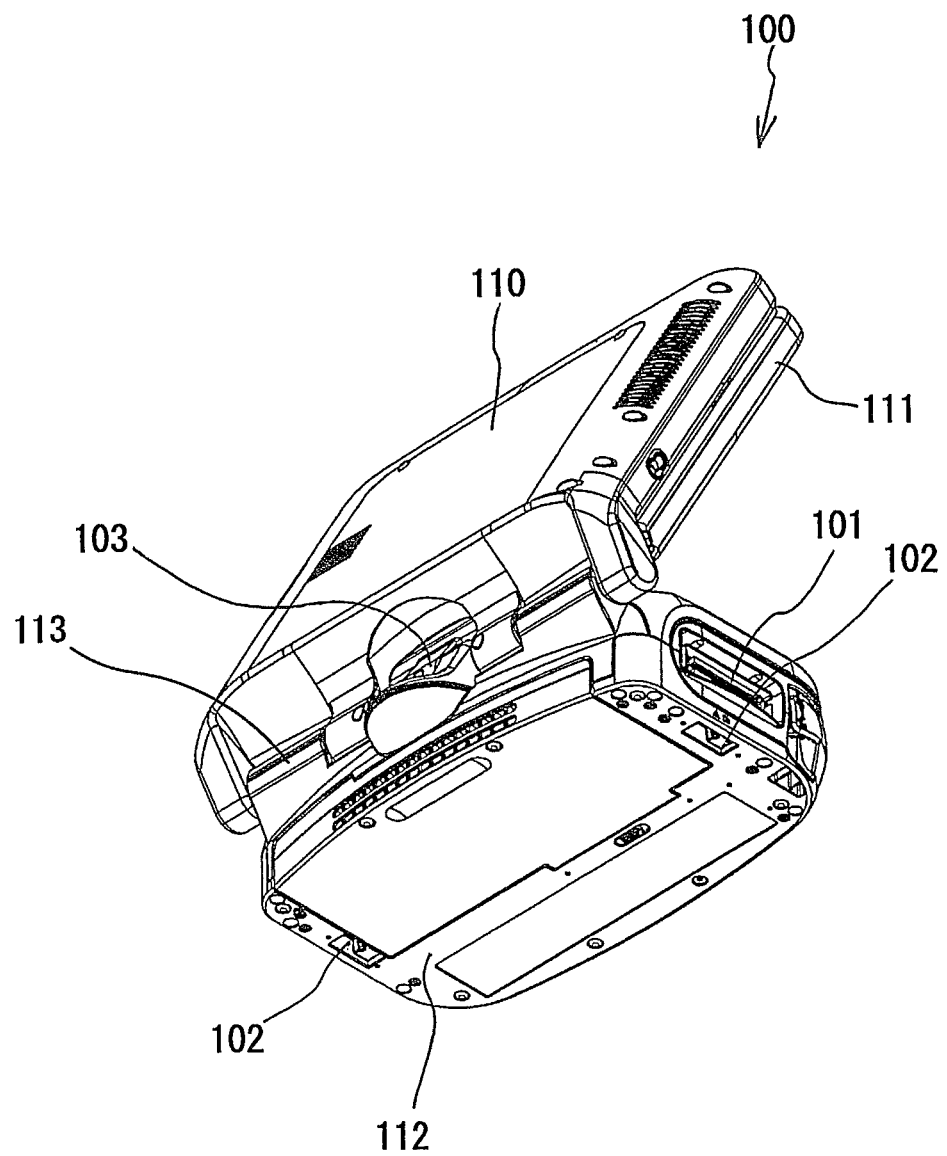
FIG. 14 is a bottom view of the portable ultrasonic diagnostic device 100.
Figure 15:
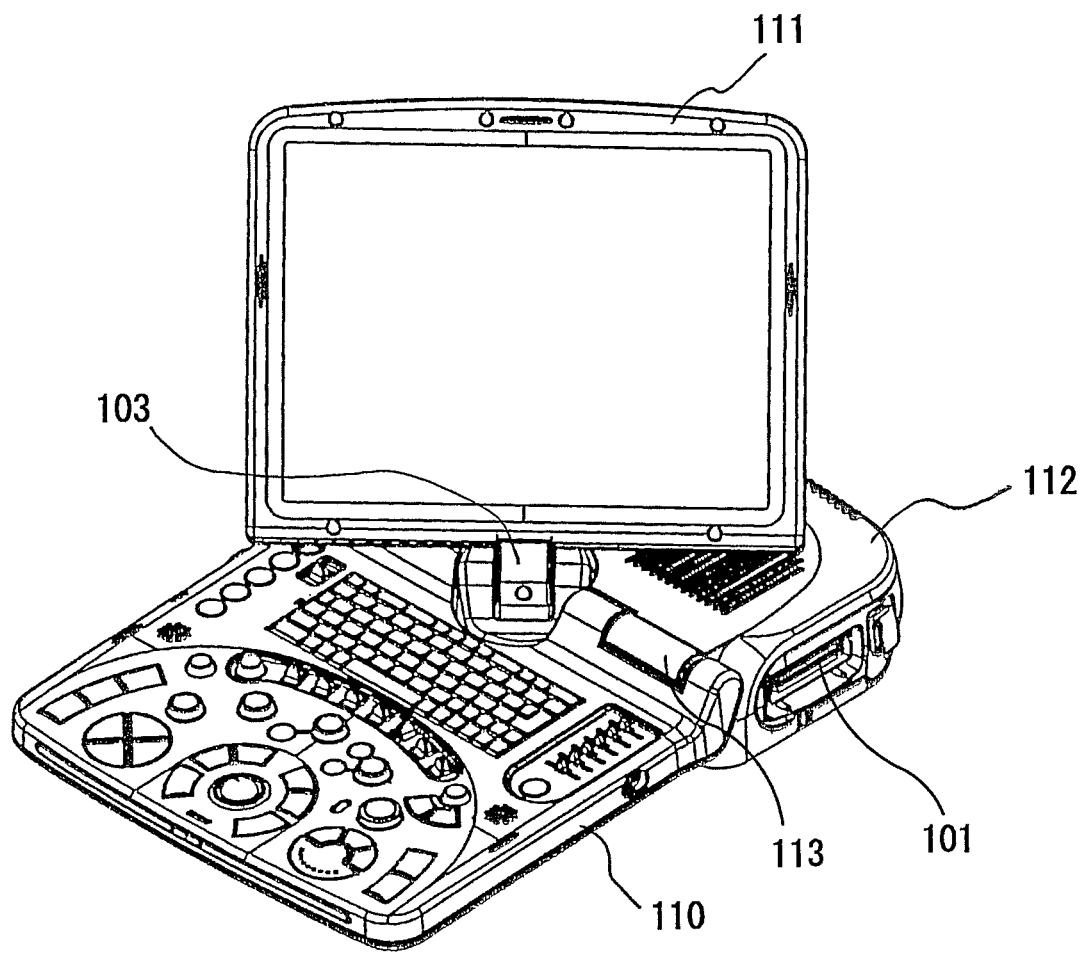
FIG. 15 is a perspective view of the portable ultrasonic diagnostic device 100 in the state that the display 111 swivels in the horizontal direction.
Figure 16:
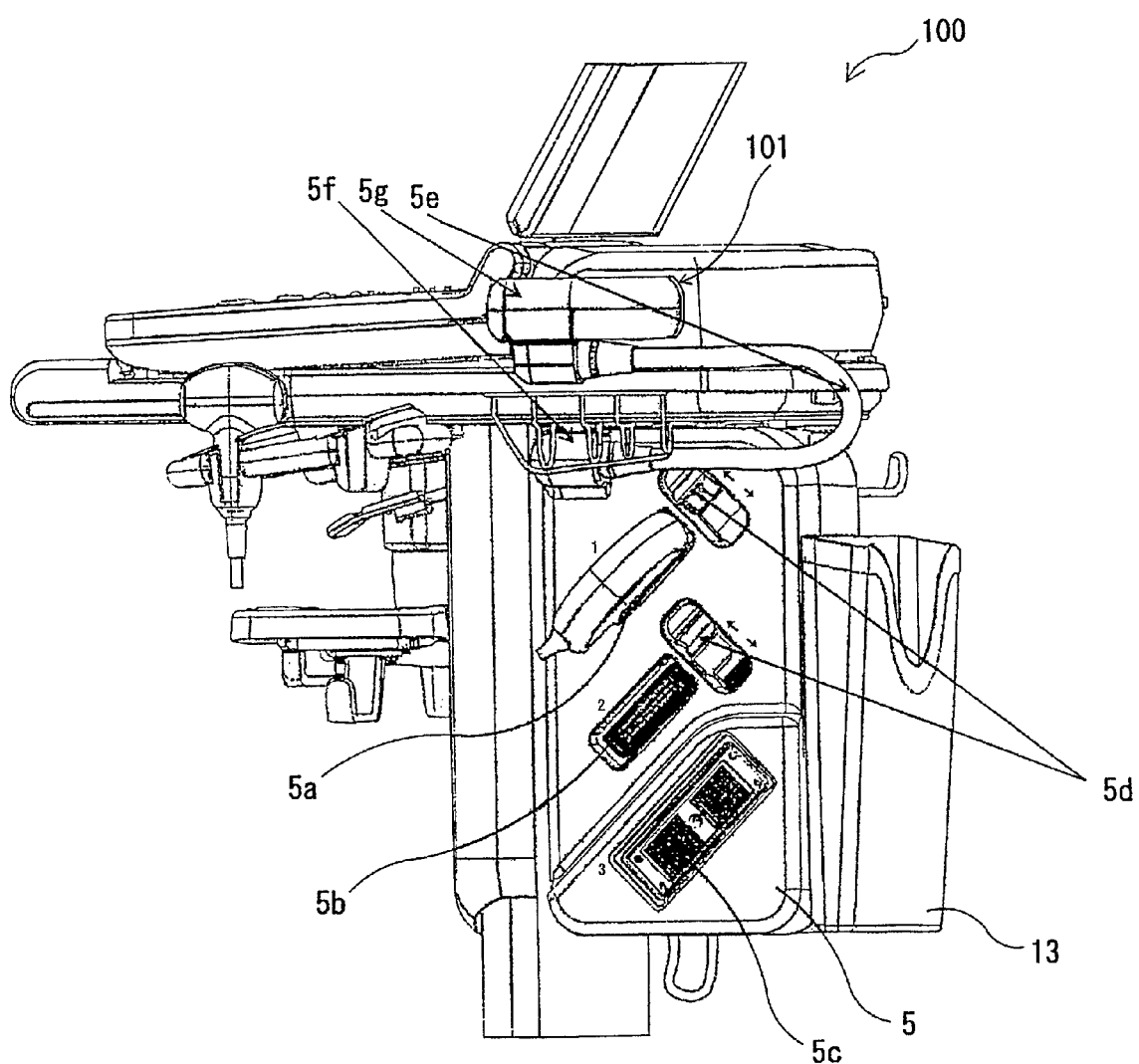
FIG. 16 is a right side perspective view in the state that the portable ultrasonic diagnostic device 100 is mounted on the cart 10 and connected via a connector.

FIG. 14 is abase view of the portable ultrasonic diagnostic device 100. FIG. 15 is a perspective view of the portable ultrasonic diagnostic device 100 in the state that the display 111 swivels in the horizontal direction. FIG. 16 is a right-side perspective view illustrating that the portable ultrasonic diagnostic device 100 is mounted on the cart 10 and connected via a connector.

As shown in the figures from FIG. 1 to FIG. 13, as a configuration of the cart 10 of the present embodiment, it is provided with the top board 1 for mounting the portable ultrasonic diagnostic device 100 thereon, the support column 2 for supporting the top board 1, the multiple legs 3 attached to the lower end of the support column 2, and the wheels 4 respectively attached to the legs 3.

As shown in the figures from FIG. 11 to FIG. 15, the portable ultrasonic diagnostic device 100 is a notebook PC type, having the display 111, the operating portion 110 such as a keyboard, a main body 112, and a probe not illustrated. The display 111, the operating portion 110, and the main body 112 are connected mutually via hinges 103 and 113, and an one-axis hinge, not illustrated. The mechanism of the hinges 103 and 113 and the one-axis hinge allow the following postures to be taken; a posture where the display 111 is placed over the operating portion 110 in a horizontal position (closed state 1), a posture where the operating portion 110 and the display 111 are put together and they are raised vertically as shown in FIG. 11 (closed state 2), a posture where the operating portion 110 is placed horizontally and the display 111 is opened and raised vertically as shown in FIG. 9 (use state 1), and a posture where the display 111 is made to swivel in the horizontal direction from the use state 1, as shown in FIG. 15 (use state 2).

As shown in FIG. 14, the bottom surface of the portable ultrasonic diagnostic device 100 is provided with a pair of concave portions 102 and a catching part arranged in each of the concave portions 102. As shown in the figures from FIG. 1 to FIG. 7, the upper surface of the top board 1 of the cart 10 is provided with convex portions 6, each having the shape being associated with the concave portion 102 on the bottom surface of the portable ultrasonic diagnostic device 100. A hook having a curved shape (not illustrated) is accommodated inside the top board 1. There is provided on the left-side surface of the top board 1, a lever 7 for turning the hook and projecting it from the top of the convex part 6. Therefore, the operator mounts the portable ultrasonic diagnostic device 100 on the top board 1, and aligns and inserts the convex portions 6 into the concave portions 102 of the bottom surface of the portable ultrasonic diagnostic device 100, thereby positioning the portable ultrasonic diagnostic device 100. Under this condition, when the lever 7 is turned, the curved hook accommodated in the top board 1 protrudes with turning, from the upper surface of the convex portion 6, and engages in the catching part within the concave portion 102 of the portable ultrasonic diagnostic device 100. With this configuration, as shown in the figures from FIG. 9 to FIG. 12, it is possible to fix the portable ultrasonic diagnostic device 100 on the upper surface of the top board 1.

As shown in the figures from FIG. 3 to FIG. 7, an extension unit 5 is fixed on the back surface of the support column 2. As shown in the figures, FIG. 4, FIG. 6, FIG. 7, and FIG. 16, there are provided on the right surface of the extension unit 5, multiple probe connectors 5a, 5b, and 5c, and a probe connector inserter/ejector lever 5d. The multiple probe connectors 5a to 5c are connectors for establishing connection with a probe (e.g., the probe 11 in FIG. 7). The probe connectors 5a, 5b, and 5c are formed at a slant, in order to facilitate cable routing of a probe cable and a connection cable. The probe connected to any of the probe connectors 5a and 5b is inserted or ejected by operating the probe connector inserter/ejector lever 5d. One end 5f of the cable 5e is connected to the right side surface of the extension unit 5. An extension unit connector 5g is provided on the other end of the cable 5e, and the extension unit connector 5g is connected to a probe connection terminal 101 of the portable ultrasonic diagnostic device 100. With this configuration, it is possible to connect multiple probes to the portable ultrasonic diagnostic device 100 via the extension unit 5.

There are mounted probe holders 12 each having at least one opening for inserting the probe, on both sides of the lower surface of the top board 1. The probe holder 12 allows insertion of the probe directly connected to the portable ultrasonic diagnostic device 100, and the probe 11, connected to the extension unit 5 and the like. The height of the probe holder 12 is determined in such a manner that the probe inserted into the probe holder 12 may not protrude upper than the top surface position of the operating portion 110 in the posture where the display 111 is opened (use state 1) as shown in FIG. 9 and FIG. 10. With this configuration, the tip of the probe may not come into contact with the hand of the operator who manipulates the operating portion 110. In addition, maintaining the probe at this position may prevent the probe from interfering with viewing the display 111, even in the case where the display 111 swivels in the horizontal direction as shown in FIG. 15.

The probe holders 12 are mounted in such a manner as leaning forward, so as to facilitate taking out the probe from the front.

The support column 2 is provided with an upper support column 2a, a lower support column 2b, and a gas damper placed inside of those elements. The upper support column 2a has a large width being equivalent to the width of the extension unit 5. The thickness (depth) of the upper support column 2a in the front-back direction is thinner than the width. Both the width and the thickness in the front-back direction of the lower support column 2b are slightly smaller than those of the upper support column, establishing a structure that the support column 2 expands and contracts by inserting the lower support column 2b into the upper support column 2a.

Since the extension unit 5 is placed in the rear (on the back surface side) of the support column 2, it is possible to leave wide space in front of the support column 2. With this configuration, the operator of the portable ultrasonic diagnostic device 100 is allowed to insert his or her knees into the front space of the support column 2, when the operator carries out an operation with standing in front of the cart 10. Therefore, the operator is allowed to stand in a natural attitude in the close vicinity of the cart 10, facilitating the operation of the portable ultrasonic diagnostic device. Additionally, the wide space in front of the support column 2 is also utilized to allow the cart 10 to be positioned in the close vicinity of the test object, and it is possible to acquire an ultrasonic image of the test object even in narrow space.

In addition, there is provided a tray 15 for putting equipment and the like, in the upper space, where the operator's knees do not hit, within the wide space in front of the support column 2. Under the tray 15, there is provided a hook 15a for hooking the cable of the probe, or the like, for routing the cable therethrough.

On the back surface of the extension unit 5, a pocket 13 is fixed for putting documents such as medical records therein.

As thus described, the extension unit 5 being heavy and the pocket 13 for putting documents therein are positioned on the back surface side with respect to the support column 2, and therefore, the center of gravity 31 of the cart 1 is positioned on the back surface side with respect to the center 2c of the support column 2, as shown in FIG. 3. In other words, the center of gravity 31 of the cart 1 is positioned on the back surface side, leaving the space in the front, thereby providing the cart being convenient which allows the operator's knees to insert therein, or allows the cart to be close to the test object. In addition, the wide space positioned in front of the support column 2 is utilized to place the tray 15 in the upper space that does not interfere with knees, and this makes space for placing equipment and enhances the convenience.

The support column 2 is configured to have a large width, and this allows the top board 1 to keep stable even though the center of gravity 31 is positioned in the rear. In addition, since the support column 2 has a width being equivalent to that of the extension unit 5, the extension unit 5 and the pocket 13 are invisible from the front, providing excellence in design.

The support column 2 is further provided with a lifting lever 14 for releasing the operation of the gas damper, in the forward part on the left side below the top board 1. When the operator grasps lightly both the lifting lever 14 and the top board 1, in such a manner as placing them between fingers, and lifts up the top board while releasing the gas damper with raising the lever, the support column 2 urged upwardly by the gas damper is extended and the top board 1 moves easily to the upper side. When the operator pushes down the top board 1 to the lower side, while releasing the gas damper by raising the lifting lever 14, the support column 2 is contracted, thereby reducing the height of the top board 1. When the operator releases his or her hand from the lifting lever 14, the length of the support column 2 is fixed, thereby fixing the position of the top board 1.

The gas damper is designed in such a manner that its spring strength approximately balances with the total weight of the top board 1, the extension unit 5, and the portable ultrasonic diagnostic device 100 supported by the support column 2. With this configuration, when the operator raises the lifting lever 14 for releasing and applies only a little force, this enables raising or pushing down the top board 1 lightly, thereby adjusting the position of the top board finely.

Since the lifting lever 14 is positioned in the forward part of the support column 2, below the top board 1 where the center of gravity 31 does not exist, the operation for raising the top board 1 and the operation for pushing down the top board 1 may not easily disturb the stability of the cart 10, and therefore a stable operation is achieved.

Since the lifting lever 14 is placed at the position manually operable by the operator's hand (below the top board 1), the operator rarely loses his or her posture upon operating the lever, relative to the configuration in which a lever is arranged in proximity to the legs 3 to be operated by the operator's foot, and the operator is allowed to adjust the height of the top board 1 delicately. By way of example, if the lever is operated by the operator's foot, the operator has to stand on one foot and operate the lever by the raised foot. Therefore, drastic motion with a large weight shift is required between the ON operation by stepping on the lever and the OFF operation by taking the foot off the lever, resulting in that delicate adjustment of the height of the top board 1 becomes difficult. On the other hand, in the present embodiment, since the top board 1 is moved up and down simultaneously with the operation of grasping and raising the lifting lever 14 by the operator's hand (ON) or with the operation of releasing the hand (OFF), there is no weight shift or posture change in the operator, enabling fine adjustment of the height of the top board 1.

The legs 3 coupled to the lower portion of the support column 2 are configured in such a manner that the number of the legs on the rear side is larger than the number of the legs on the front side. In addition, the length of the legs on the rear side from the center 2c of the support column 2 is designed to be longer than the length of the legs on the front side. This configuration allows the center of gravity 31 positioned in the rear to be supported by the legs on the rear side, thereby supporting the entire cart 10 stably.

Since the lifting lever 14 is placed below the top board 1, the legs 3 are not provided with any operating portion. Therefore, it is possible to mount the trays 16 and 17 respectively on the legs 3 of the front side and the rear side, as needed. Necessary equipment is put on the trays 16 and 17, enhancing the convenience furthermore. The tray 16 on the front side is designed in the size that may not interfere with the operator's legs.

The top board 1 is provided with the palm rest 9 that is slidable forwardly. The front of the palm rest 9 is formed in the shape of a handle. A lock part 9a is provided inside the handle of the palm rest 9. The lock part 9a is a mechanism that fixes both the state as shown in FIG. 11 and FIG. 12 before the palm rest 9 is pulled out, and the state as shown in the figures from FIG. 3 to FIG. 10 in which the palm rest 9 is pulled out. In the case of pulling out the palm rest 9, the operator draws the lock part 9a to release the lock, and then pulls out the palm rest. When the palm rest comes into the state of being pulled out to the utmost limit, as shown in the figures FIG. 3 to FIG. 10, the palm rest 9 is locked mechanically, and it is fixed in the state being pulled out, until the lock part 9a is released again. If the palm rest 9 is put into the top board 1 from the state being pulled out, the lock part 9a is released and the palm rest 9 is pushed into the top board 1. When the palm rest 9 comes into the state being inserted in the top board 1 as shown in FIG. 11 and FIG. 12, the palm rest is locked again mechanically and fixed until the lock part is released.

With this palm rest 9 being provided, it is possible to set the size of top board 1 in the depth direction to be smaller than the total size in the depth direction of the operating portion 110 and the main body 112 of the portable ultrasonic diagnostic device 100. Therefore, this may achieve a compact cart 10. Upon placing the operating portion 110 horizontally as shown in FIG. 9 and FIG. 10 to manipulate the operating portion 110, the palm rest 9 is pulled out. With this configuration, the palm rest 9 protrudes in front of the operating portion 110, allowing the operator to carry out operation with putting his or her hand on the palm rest 9. Since the portable ultrasonic diagnostic device 100 is small in size, manual operation buttons, and the like, are arranged fully on the upper surface of the operating portion 110. In this situation, the operator is allowed to put his or her wrist stably on the palm rest 9, upon manipulating the operation buttons positioned at the forward end, and therefore the operability is enhanced drastically.

Since the palm rest 9 is provided with the shape of a handle, this shape allows the operator to grasp the handle and turn the cart 10 around, or take an action to put the cart closer to the operator or the test object, while keeping the state that the palm rest is pulled out as shown in FIG. 9 and FIG. 10. As shown in FIG. 11 and FIG. 12, when the operating portion 110 and the display 111 of the portable ultrasonic diagnostic device 100 take a posture being put together and set up approximately vertically, and the palm rest 9 is inserted into the top board 1, the operator is allowed to grasp the handle of the palm rest 9, and push the cart 10 and walk, just like pushing a dolly. This configuration allows the cart 10 to move for a long distance at a walking speed, while keeping the portable ultrasonic diagnostic device 100 being mounted.

As described above, with the palm rest 9 having the shape of a handle, this handle is usable not only as a palm rest originally intended for putting a hand thereon, but also as a handle for turning the cart 10 around and as a handle for walking with pushing the cart like a dolly. Therefore, this enhances the convenience as the cart for the ultrasonic diagnostic device.

According to the present invention, it is possible to provide a cart being small in size and having high operability, suitable for mounting a portable ultrasonic diagnostic device with a simple configuration. Mounting the portable ultrasonic diagnostic device on this cart not only facilitates moving, but also allows the portable ultrasonic diagnostic device to be opened and used while it is kept mounted on the cart. In addition, since there is wide space in front of the support column of the cart, when the operator stands in front, his or her knees is allowed to be inserted therein, and this enables the operator to carry out operation comfortably in a posture being suitable for easy operation. Since there is large space in front of the cart, it is possible to place the cart close to the test object, and even when there is not large space around the test object, this small-sized cart is allowed to be placed while approaching the test object, and an ultrasonic image may be obtained by bringing the probe into contact with the test object. Therefore, even in the space where approaching by a large-sized mobile ultrasonic diagnostic device is difficult, it is possible to conduct ultrasonic diagnosis by mounting the portable ultrasonic diagnostic device on the cart according to the present embodiment.

In the embodiment as described above, the portable ultrasonic diagnostic device 100 is configured in such a manner as attachable to and detachable from the top board 1 of the cart 10. It is further possible to establish a structure that the portable ultrasonic diagnostic device 100 is fixed in advance integrally to the top board 1.

Through the aforementioned cart 10 has a configuration that the extension unit 5 for installing an additional probe is provided, it is further possible to provide a unit having a different function, instead of the extension unit 5. By way of example, instead of the extension unit 5, an accessory case may be provided for putting in documents such as medical records, or appliances.

EXPLANATION OF REFERENCES

1: top board, 2: support column, 3: legs, 4: wheels, 5: extension unit, 6: convex portion, 7: lever, 9: palm rest, 10: cart, 12: probe holder, 13: pocket, 14: lever, 15: tray, 15a: hook, 16, 17: tray, 100: portable ultrasonic diagnostic device, 101: probe connection terminal, 103: hinge, 110: operating portion, 111: display, 112: main body

What is claimed is:

1. A cart for a portable ultrasonic diagnostic device, comprising,
   a top board for attachably and detachably placing the portable ultrasonic diagnostic device thereon,
   a support column for supporting the top board in such a manner as being movable up and down,
   multiple legs for supporting the support column, wheels respectively attached to the legs, and
   a unit having a predetermined function, wherein,
   the unit being placed below the top board in a rear of the support column, and regardless of whether the portable ultrasonic diagnostic device is mounted on the ton board or not, a center of gravity of the cart being positioned in a rear of a center of the support column; and
   the portable ultrasonic diagnostic device has a main body, an operating portion and a display, the operating portion and the display are positioned forward of the main body
   an upper surface of the top board is provided with a convex portion for engaging with a concave portion provided on a bottom surface of the main body of the portable ultrasonic diagnostic device,
   the top board is provided with a hook which is accommodated in the top board in such a manner as protrudable from the upper surface of the top board, the hook being engaged with the bottom surface of the main body of the portable ultrasonic diagnostic device, in order to fix the portable ultrasonic diagnostic device on the top board, and
   while the main body being fixed to the top board. the operating portion and the display are configured to be held at a raised state.

2. The cart for the portable ultrasonic diagnostic device according to claim 1, further comprising,
   a lifting lever for controlling up-and-down movement of the top board, wherein,
   the lifting lever is arranged at a position around the top board, forward of the support column, where the center of gravity of the cart is not located.

3. The cart for the portable ultrasonic diagnostic device according to claim 1, wherein,
   the number of the legs positioned rearward of the support column is larger than the number of the legs positioned forward thereof.

4. The cart for the portable ultrasonic diagnostic device according to claim 1, further comprising a palm rest which is provided being slidable outwardly, on the front side of the top board and which has a handle provided on the front of the palm rest,
   the size of the top board in a depth direction is smaller than a total size in a depth direction of the portable ultrasonic diagnostic device,
   upon placing the portable ultrasonic diagnostic device on the top board. the palm rest is pulled out to support the operating portion of the portable ultrasonic diagnostic device, and
   the handle is exposed in front of the top board when the palm rest is accommodated into the top board.

5. The cart for the portable ultrasonic diagnostic device according to claim 4, further comprising a lock mechanism for fixing each of following states; the state in which the palm rest is pulled out from the top board, and the state in which the palm rest is accommodated in the top board.

6. The cart for the portable ultrasonic diagnostic device according to claim 1, wherein,
   the support column has a flat shape in which a column width is larger than a column depth.

7. The cart for the portable ultrasonic diagnostic device according to claim 6, wherein,
   the column width of the support column is equivalent to the width of the unit.

8. The cart for the portable ultrasonic diagnostic device according to claim 1, further comprising a probe holder which is placed around the top board, for holding a probe of the portable ultrasonic diagnostic device, wherein,
   the probe holder is arranged in such a manner that an upper end of the probe to be held is positioned lower than the upper surface of an operating portion of the portable ultrasonic diagnostic device that is placed on the top board.

9. An ultrasonic diagnostic unit comprising, a portable ultrasonic diagnostic device, and
   a cart for mounting the portable ultrasonic diagnostic device thereon, the cart being described in claim 1.

* * * * *